United States Patent
Xia et al.

(10) Patent No.: US 10,073,005 B2
(45) Date of Patent: Sep. 11, 2018

(54) DISTRIBUTED NONDESTRUCTIVE STRUCTURAL DEFECTS DETECTION IN SLICKLINE CABLES

(71) Applicant: Halliburton Energy Services, Inc., Houston, TX (US)

(72) Inventors: Hua Xia, Huffman, TX (US); David L. Perkins, The Woodlands, TX (US); John L. Maida, Houston, TX (US); Sean Gregory Thomas, Frisco, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 140 days.

(21) Appl. No.: 15/116,464

(22) PCT Filed: Jun. 16, 2014

(86) PCT No.: PCT/US2014/042500
§ 371 (c)(1),
(2) Date: Aug. 3, 2016

(87) PCT Pub. No.: WO2015/195074
PCT Pub. Date: Dec. 23, 2015

(65) Prior Publication Data
US 2017/0010181 A1   Jan. 12, 2017

(51) Int. Cl.
| | |
|---|---|
| G01N 21/00 | (2006.01) |
| G01M 11/08 | (2006.01) |
| E21B 47/12 | (2012.01) |
| G01B 11/16 | (2006.01) |
| G01M 11/00 | (2006.01) |
| E21B 47/00 | (2012.01) |
| G01V 8/10 | (2006.01) |
| G01N 21/95 | (2006.01) |

(52) U.S. Cl.
CPC ........... G01M 11/086 (2013.01); E21B 47/00 (2013.01); E21B 47/123 (2013.01); G01B 11/16 (2013.01);
(Continued)

(58) Field of Classification Search
CPC ........ E21B 47/00; E21B 47/123; E21B 47/18; E21B 2049/085; E21B 49/08;
(Continued)

(56) References Cited

U.S. PATENT DOCUMENTS
| | | |
|---|---|---|
| 2005/0023434 A1 | 2/2005 | Yacoubian et al. |
| 2005/0135763 A1 | 6/2005 | Drenzek et al. |

(Continued)

FOREIGN PATENT DOCUMENTS
| | | |
|---|---|---|
| EP | 2278324 A1 | 1/2011 |
| WO | WO-2014003859 A1 | 1/2014 |

(Continued)

OTHER PUBLICATIONS

"International Application Serial No. PCT/US2014/042500, International Search Report dated Mar. 19, 2015", 4 pgs.

(Continued)

*Primary Examiner* — Sunghee Y Gray (57) ABSTRACT

In some embodiments, a distributed nondestructive inspection method for slickline cable structural defect detection transmits a light pulse along an optical waveguide in the slickline cable. A reflected light signal is 5 received from the optical waveguide in response to the light pulse. Defects can then be determined in the slickline cable based on variations in scattering intensity, phase shift, specific spectral signature, power spectral density, strain amplitude, and/or transmission loss of the reflected light signal as compared to the light pulse.

6 Claims, 7 Drawing Sheets

(52) U.S. Cl.
CPC .......... *G01M 11/083* (2013.01); *G01M 11/31* (2013.01); *G01V 8/10* (2013.01); *G01N 2021/9511* (2013.01)

(58) Field of Classification Search
CPC ..... G01B 11/16; G01M 11/086; G01M 11/31; G01M 11/083; G01N 2021/9511; G01V 11/002; G01V 8/02; G01V 1/226; G01V 8/16; G01V 8/10; G01D 5/35364
USPC ........................................................ 356/73.1
See application file for complete search history.

(56) References Cited

U.S. PATENT DOCUMENTS

| | | |
|---|---|---|
| 2009/0157358 A1 | 6/2009 | Kim |
| 2011/0001959 A1* | 1/2011 | Hasegawa .......... G01M 11/3172 356/73.1 |
| 2012/0176250 A1* | 7/2012 | Duncan ................ G01V 11/002 340/853.2 |
| 2012/0203493 A1 | 8/2012 | Dobson et al. |
| 2013/0308137 A1* | 11/2013 | Manzke ................ G01B 11/18 356/511 |
| 2013/0342210 A1 | 12/2013 | Stokely |

FOREIGN PATENT DOCUMENTS

| | | |
|---|---|---|
| WO | WO-2015195074 A1 | 12/2015 |
| WO | WO-2015195150 A1 | 12/2015 |

OTHER PUBLICATIONS

"International Application Serial No. PCT/US2014/042500, Written Opinion dated Mar. 19, 2015", 12 pgs.

"International Application Serial No. PCT/US2014/047612, International Search Report dated Mar. 19, 2015", 4 pgs.

"International Application Serial No. PCT/US2014/047612, Written Opinion dated Mar. 19, 2015", 12 pgs.

* cited by examiner

DISTRIBUTED NONDESTRUCTIVE STRUCTURAL DEFECTS DETECTION IN SLICKLINE CABLES

PRIORITY APPLICATION

This application is a U.S. National Stage Filing under 35 U.S.C. 371 from International Application No. PCT/US2014/042500, filed on Jun. 16, 2014 and published as WO 2015/195074 A1 on Dec. 23, 2015, which applications and publication are incorporated herein by reference in their entirety.

BACKGROUND

Slickline cable, also referred to as wireline cable, can be used in a wellbore to provide downhole logging tool support and communication between the downhole environment and the surface of the well. The slickline cable can include communication cabling (e.g., fiber optics, metal conductor wires) between a wireline tool and the surface as well as the structural support to raise and lower the wireline logging tool.

Catastrophic failure of a composite material based slickline cable can be a result of continuous degradation of the cable mechanical strength, induced by a geological formation, and subsequent propagation of the various structural defects during downhole tool loading or service time. The wireline logging tool loading may produce either static tensile stress or transient tensile stress along the slickline cable. Specifically, the transient tensile stress event may lead to formation of various internal structural defects, such as cracking and delamination. Such structural defects may be localized and may not show obvious influence on cable performance at initial status. However, a percolation threshold can be trigged by continuous tensile stress loading. The initial nano-structural or micro-structural defects may grow along the loading axis, and propagate quickly, resulting in the slickline cable having non-uniform stress loading.

Existing nondestructive inspection technologies, such as laser ultrasonic, transient thermography, eddy current, or x-ray radiography, are useful during manufacture of the composite material based slickline cable but are difficult to be implemented in the downhole environment for real-time monitoring and diagnosis of potentially catastrophic slickline cable failures. In addition, these conventional nondestructive inspections are single-point analytical technique and difficult to effectively scan structural defects along full length of the slickline cable within limited time. There are resulting needs to detect slickline cable structural defects along full length of ~30,000 ft in a downhole environment.

DETAILED DESCRIPTION

Polymer composite materials typically include reinforcement material such as carbon, glass, ceramic, or optical fibers, which are embedded in a polymeric matrix material (e.g., thermoplastic resin). The advantages of fiber-reinforced polymer composite materials based cable over a metal cable can include improved toughness, lower weight, and increased resistance to fatigue and corrosion. Polymer composite materials, however, can develop internal structural defects (e.g., fiber or matrix cracking, delamination, voids etc.) at loads far below their failure stress. Such structural defects may not show significant impact on the cable mechanical strength at the initial defect formation stage but the relatively rapid growth and propagation of these structural defects could lead to catastrophic failure. This is especially true when these cracking and delamination defects grow radially.

Initial nano- or micro-structural defects may be introduced by the manufacturing process but magnified by transient inhomogeneous loading stress from downhole logging tools. As the downhole logging tool loads on polymer composite material based slickline cable increase, the effective mechanical strength can be gradually decreased with repeated loading due to plastic deformation, which depends upon the internal structural defect formation, growth and propagation. The service lifetime of a slickline cable can depend on the orientations of internal structural defect growth and propagation either along axial or radial directions or in-between. Although keeping the downhole logging tool loading under 10-30% of the designed full capability could be a practical slickline cable reliability control method, the transient loading induced non-uniform stress is often difficult to be controlled and may lead to radially grown cracks or delamination defects.

To address some of the challenges described above, as well as others, apparatus, systems, and methods for performing structural defect detection in slickline cables are presented. A structural defect detection system can include a light source (e.g., near-infrared), a picosecond gating electronic circuitry, and signal process circuitry. Such a structural defect detection system can be installed near a wellhead with slickline cable spooling from a reel to the downhole environment.

Transient and non-uniform loading induced structural defects can emit acoustic noises or localized strain waves that are analyzed either in the time-domain or in the frequency-domain by coherent interference techniques that measure coherent light-scattering from optical waveguide(s). Structural defects, such as micro-cracking and micro-delamination, can be identified by their modulation on the refractive index of the optical waveguide(s). In the time-domain, the localized strain field will lead to phase shift by $\in(t)=\Delta\Phi(t)/\Phi$; while its Fast Fourier Transform will give power spectral density that could allow one to identify specific spectral signature(s) from structural defects creation process. However, a down-shift of a specific spectral signature in the power spectral density may be associated indirectly with slickline cable mechanical strength fatigue or directly with structural defect growth and propagation.

To measure structural defects from an optical waveguide(s) or fiber(s) embedded polymer composite cable, a coupling method is disclosed for using optical waveguide(s) to sense structural defect induced acoustic signals that propagate inside the composite cable based acoustic waveguide. The structural defect induced dynamic strain signals can lead to refractive index variations of the optical waveguide(s) that are analyzed by the localized strain amplitude, the spectral signature(s) in the power spectral density, and the spectral signature(s) shift trend. These parameters can be used to identify structural defect formation, growth rate, and propagation in the slickline cable. The criteria for identifying slickline cable failure modes can focus on the defect growth rate that may be associated with increasing strain amplitude, acoustic resonant power spectral density, and on potential catastrophic failure event that could be associated with downshift trend of the specific spectral signature(s) in the power spectral density.

Figure 1:
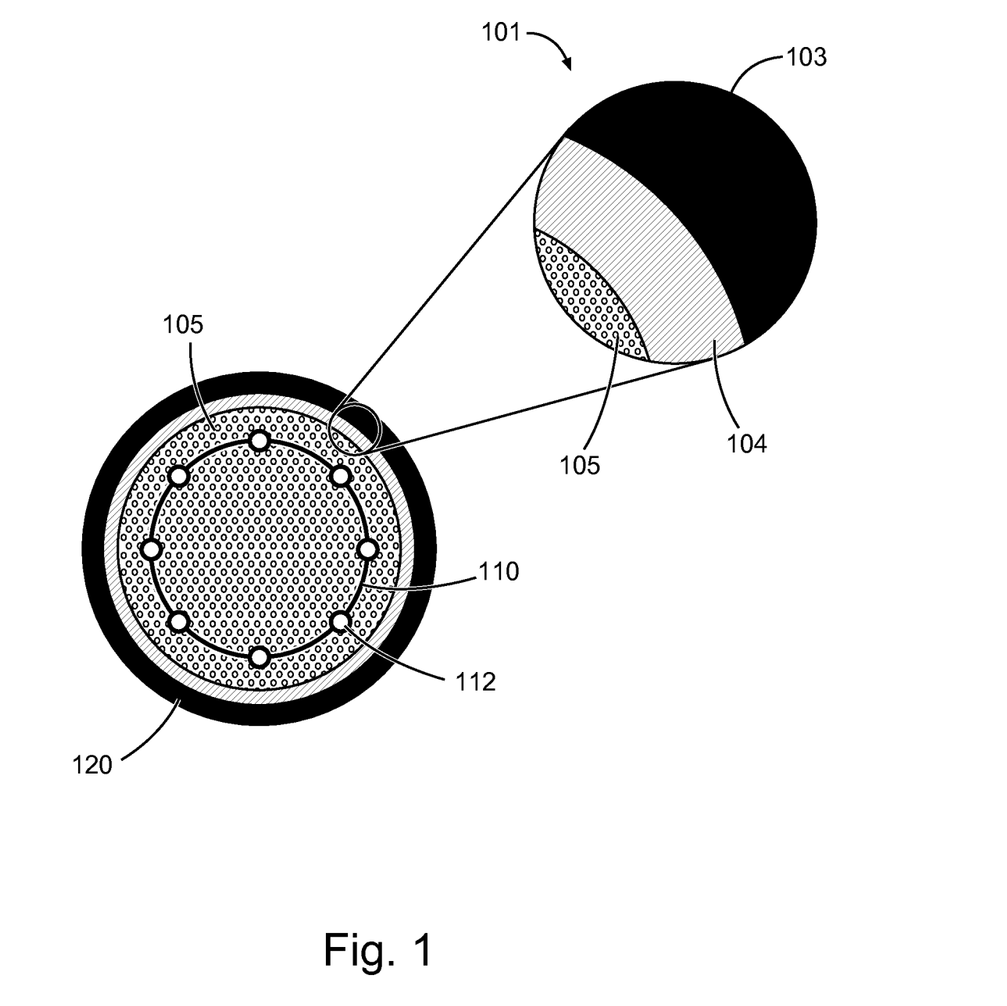
FIG. 1 illustrates a cross-sectional view of an embodiment of a slickline cable with acoustic waveguide structure and with embedded optical waveguide structures.

FIG. 1 illustrates a cross-sectional view of an embodiment of a slickline cable with acoustic waveguide structure and embedded optical waveguide structures. A more detailed cross-sectional view 101 that focuses on the outer layers is also shown. These cross-section views are for purposes of illustration only as other embodiments can include different slickline structures.

The detailed view 101 shows a double layered high-shear-modulus material that includes a composite material outer protection layer 103 and an inner hard-shear modulus layer 104. These outer layers 103, 104 can be considered as an acoustic waveguide 120. An acoustic wave may be guided by the double layered because of reflection at mismatched impedance interface.

The hard-shear-modulus layer 104 can have an elastic shear modulus, G, that is greater than that of a composite material (e.g., carbon fiber-embedded, polymeric matrix material) 105. The hard-shear modulus layer 104 can provide a reflection boundary for guided acoustic waves. The acoustic waveguide 120 can be used for localized acoustic signal reflection and transmission. The hard-shear modulus layer may be a carbon fiber reinforced PEEK or high-percentage carbon fiber filled PSS polymer. One embodiment is the ratio of the acoustic impedance of outside hard-shear-modulus layer and the internal composite material is at least between 3 and 5, and the other embodiment, this ratio is between 5 and 10.

The optical waveguides 110 are embedded into the composite cable based acoustic waveguide 120 with mechanical coupling provided by a carbon fiber-reinforced polymeric matrix 105. In one embodiment the optical waveguide 110 includes a plurality of optical fibers 112 formed in a ring within the polymeric matrix 105. In other embodiment the optical waveguide 110 includes a plurality of optical fibers 112 formed in a random pattern (not shown) within the polymeric matrix 105. In also another embodiment at least one optical waveguide is embedded inside the polymer matrix.

Figure 6:
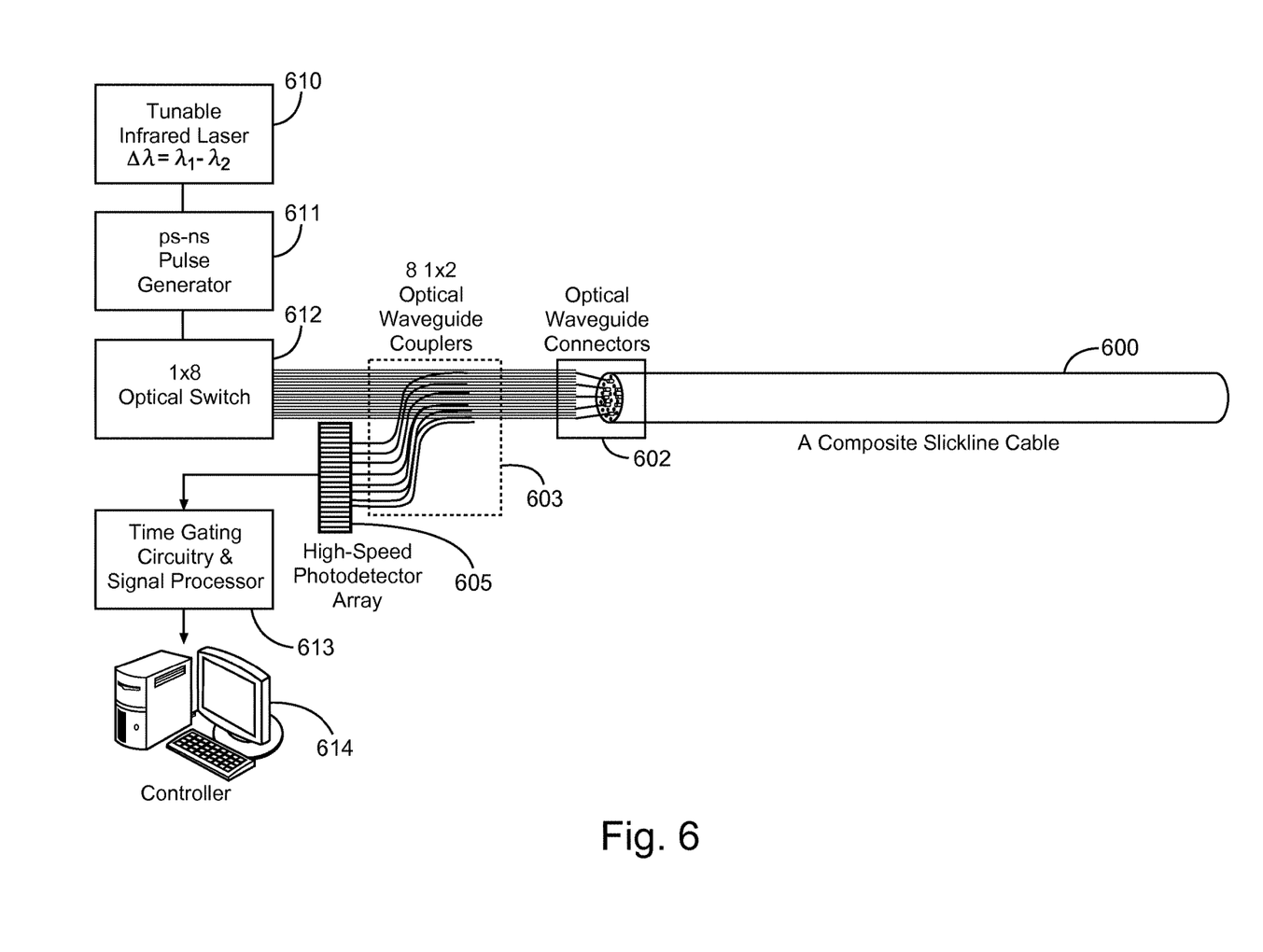
FIG. 6 illustrates a block diagram of an embodiment of a structural defects detection system.

The measured initial light transmission loss value from each slickline cable is a function of the distance from the downhole environment to the surface system (as seen in FIG. 6). The sum of the measured transmission losses from the optical waveguides can be dependent upon optical waveguide breakage or localized cable crack induced localized strains.

Figure 2:
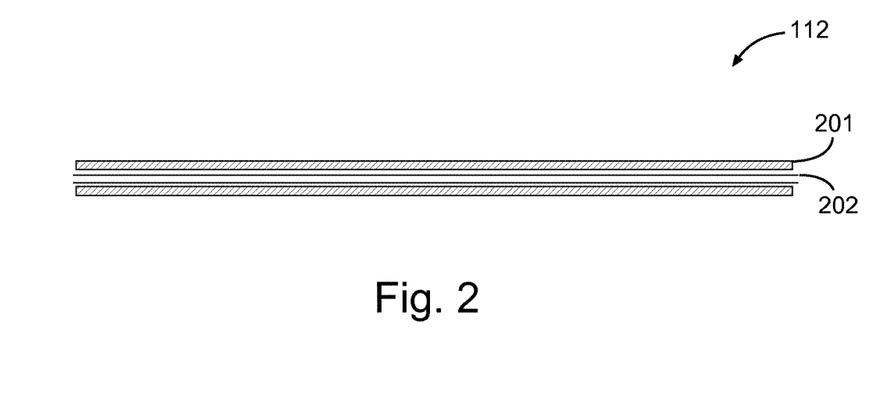
FIG. 2 illustrates an embodiment of an optical waveguide structure in accordance with the embodiment of FIG. 1.

FIG. 2 illustrates an embodiment of an optical fiber 112 (e.g., waveguides) for the optical waveguide structure 110 in accordance with the embodiment of FIG. 1. The optical waveguide structure 110 includes single mode optical fibers 112 that comprise fluorine-doped silicon dioxide cladding 201. The fiber core 202 can comprise 4-10 µm diameter pure silicon dioxide with step-refractive index profile. In another embodiment, the optical waveguide structure 110 can comprise multimode optical fibers 112 that can comprise fluorine-doped silicon dioxide double-cladding 201 while the fiber core 202 includes 50-62.5 µm diameter pure silicon dioxide either with a step refractive index profile or with gradient refractive index profile.

The multimode optical fibers cladding 201 has a jacketing layer, either a polyimide or a carbon layer of 10-20 µm thick. In one embodiment, the multiple optical waveguides can be used to measure transmission loss for evaluating potential radial crack defect formation. In another embodiment, the use of the multiple optical waveguides can detect a strongly localized defect formation event across the whole slickline cable medium.

Figure 3:
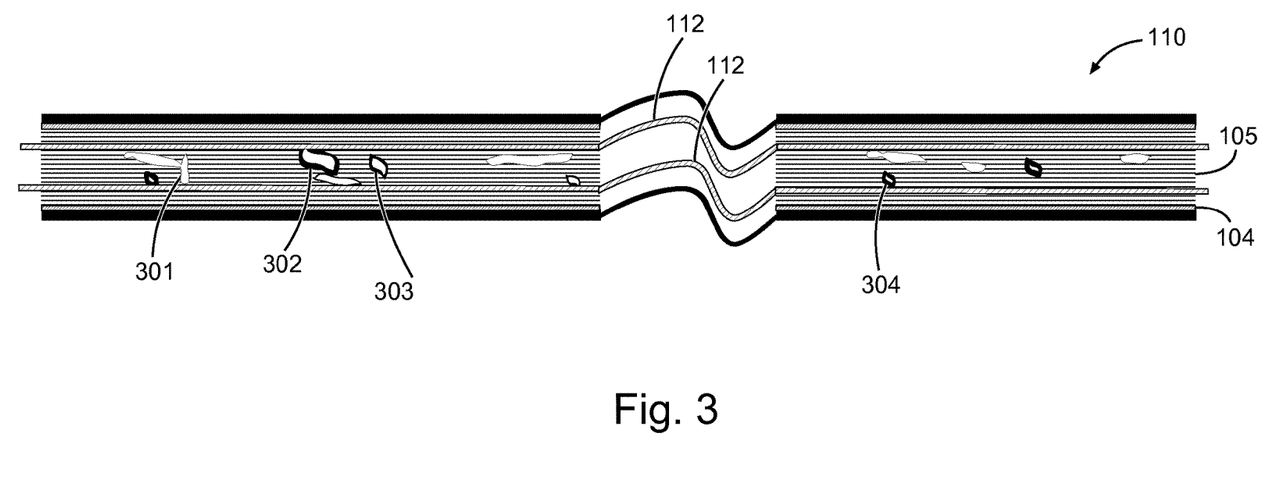
FIG. 3 illustrates an embodiment of an acoustic waveguide structure with embedded optical waveguides and possible structural defects in accordance with the embodiment of FIG. 1.

FIG. 3 illustrates a detailed acoustic waveguide structure 110 with the embedded optical fibers 112 (e.g., waveguides). Carbon fibers are embedded into and part of the polymeric matrix material 105 and protected by the hard shear material 105. The hard shear material 105 can include materials such as polyetherketone (PEEK), carbon fiber doped polyetherketone (c-PEEK), metal-wire enhanced polyetherketone (m-PEEK), or combinations thereof.

Initial nano- or micro-structural defects 301-304 can be introduced by the manufacturing process and then magnified by transient inhomogeneous loading stress from downhole logging tools. As the downhole logging tool loading on composite materials-based slickline cables increases, the effective mechanical strength could be gradually decreased with repeated loading because of potential plastic deformation that may be attributed to the creation of the structural defects.

Figure 4:
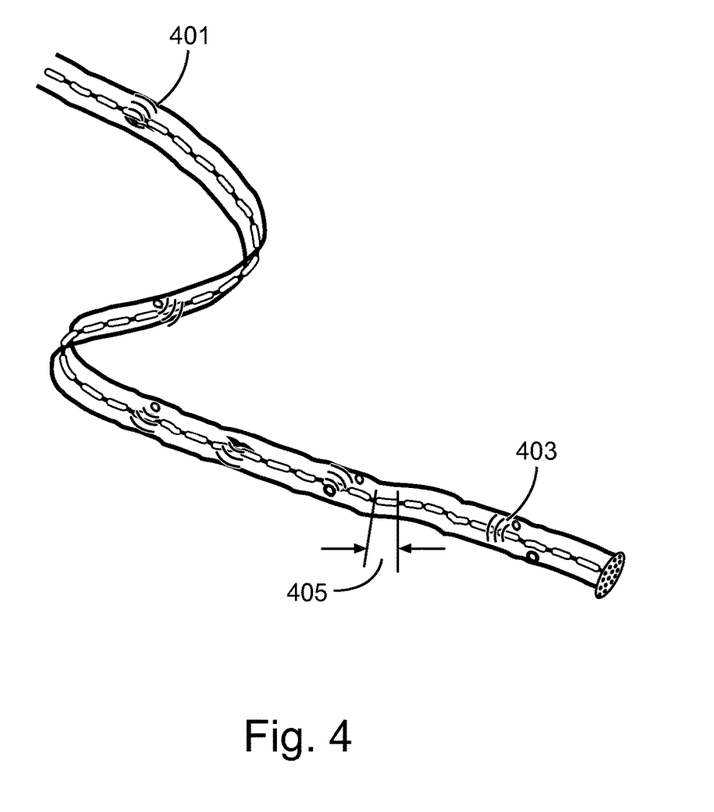
FIG. 4 illustrates a diagram of localized structural defect induced localized acoustic waves that could modulate optical waveguide refractive index variation.

FIG. 4 illustrates a diagram of localized structure defect-induced noise 401, 403 that could be produced during a wireline tool loading event. The tensile strain induced defects could be cracks, delaminations, voids, and/or fiber slips with accompanying composite material localized deformation such as bending, torsion, and buckling. The defects can occur below the maximum loading limit of a designed slickline cable. Such localized and transient acoustic waves could propagate in opposite directions 500 of a slickline cable, as shown in FIG. 5.

Figure 5:
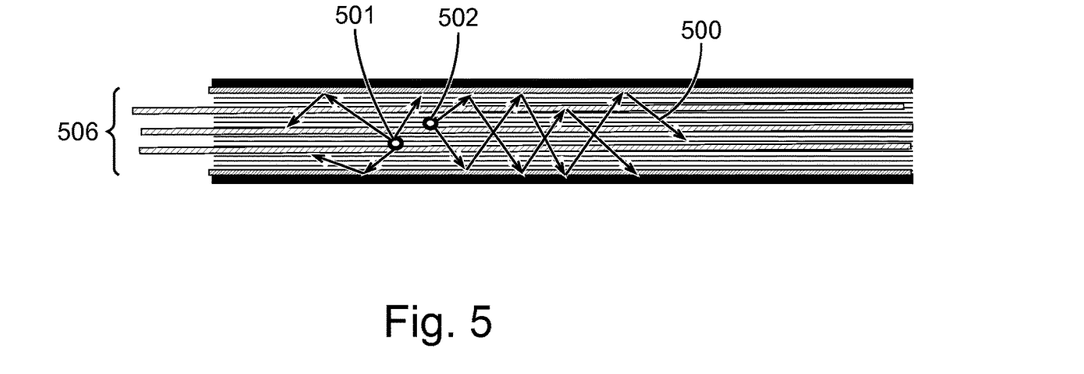
FIG. 5 illustrates a cross-sectional view of a slickline cable having localized defect induced high-frequency acoustic wave propagation around the optical waveguides.

FIG. 5 illustrates a cross-sectional view of a slickline cable having localized defect 501, 502 induced broadband acoustic wave propagation 500. The cross-sectional view illustrates multiple acoustic signal detecting lines 506 running through the cable. These lines or optical waveguides can be used by surface equipment to detect acoustic signals propagated upward or downward through the cable. The localized defects 501, 502 could modify local strain field distribution that changes refractive index of the optical waveguides. When the acoustic impedances of the outside layer 103 and internal fiber-polymer matrix material 105 (see FIG. 1) satisfy guided acoustic wave boundary conditions, the defect formation-induced mechanical deformation or acoustic waves could propagate along the slickline cable for at least a short distance before attenuated and absorbed by the polymer matrix material 105 (e.g., composite material). Corresponding to transient matrix material medium deformation, the dielectric constant or refractive index of the optical fibers could be perturbed by transient a photoelastic effect: $\Delta\Phi/\Phi \cong \Delta n/n = -(n^2/2Y) \cdot \sigma_z \cdot [(1-\nu) \cdot p_{12} - \nu \cdot p_{11}]$, where n is refractive index, $p_{11}$ and $p_{12}$ are photoelastic coefficients, $\nu$ is Poisson's ratio, and $\sigma_z$ is axial stress on the optical waveguide.

The disclosed embodiments, as shown and discussed subsequently, can enable a single optical waveguide, embedded in the center of the cable based acoustic waveguide, to detect such refractive index variation associated defect formation events. Another embodiment can use multiple optical waveguides, uniformly embedded in the cable based acoustic waveguide as multiple acoustic signal detecting strands, to detect strain induced refractive index variation associated defect formation events in order to capture the defect formation events. It may be beneficial to compare the measured acoustic signals from different optical waveguides, but at the same location, for correct data interpretation and defect identification.

FIG. 6 illustrates a block diagram of an embodiment of a slickline structural defect detection system. This system can use a coherent interference detection technique to detect localized acoustic wave-induced dielectric or refractive index variations as created by defects in the slickline cable 600. The localized refractive index variation will modulate light transmission and scattering and the measured dynamic signals could be analyzed in both time-domain and frequency-domain by a controller 614.

The system, coupled to the cable 600 through an optical waveguide connector 602, comprises a tunable laser 610 (e.g., infrared) that provides light signals to a picosecond (ps)-nanosecond (ns) pulse generator 611. The laser 610 can provide a coherent light signal in multiple wavelengths that can be used for different lengths of cable. For example, for longer cables, the light signals can be 800 nm to 1000 nm, 1000 nm to 1350 nm, 1500 nm to 1650 nm, or some other wavelength. For shorter cables, the laser 610 can generate a broad band superluminescent signal of 0.5 μm-5 μm.

The ps-ns pulse generator 611 can generate a modulated light pulse signal from the laser signal. The pulse generator can produce a typical pulse width measured in the picoseconds (ps). The modulated light pulse signal from the pulse generator 611 is input to an optical switch 612 (e.g., 1×8) or a multi-channel optical waveguide 603 that can optionally replace the optical switch 612.

For example, the optical switch/multi-channel optical waveguide 612/603 provides switching of the modulated light pulse signal amongst a plurality of optical waveguides, through optical waveguide connectors 602, for using narrow-band laser light source. As discussed and shown previously, the optical waveguides are located inside the composite slickline cable 600. In one embodiment, a single-wavelength laser beam is coupled to different optical waveguides via a 1×N optical coupler. In another embodiment, the laser beam is coupled to optical waveguides by a 1×N optical switch, where N=2, 4, 8, 16, and 32.

A photodetector array 603 is coupled to the optical waveguide connectors 602 for receiving the reflected light signals from the optical waveguides in the composite slickline cable 600. The optical couplers of the photodetector array 603 convert the received reflected and scattered light signals to electrical signals for use by time gating circuitry and signal processor 613. The multiple optical waveguide signals are picked up with the optical couplers to electronic circuitry that converts optical signal to electronic signal under precise time gating sequence for signal processing.

A picosecond-pulse light propagates along the optical waveguides at the speed of light with a coherent length defined by the laser coherent length. In one embodiment, this length can be from 0.1 meter (m) to 10 m. When the picosecond-pulsed light propagates along the waveguides of the slickline cable 600, the localized coherent interference signal is received and analyzed according a gated time sequence. The relative signal variations in the scattering intensity, phase shift, specific spectral signature, power spectral density, amplitude attenuation, and/or transmission loss characteristics are used detect and analyze the slickline cable structural defect formation, growth, and propagation. These signal variations can be determined by the controller 614 coupled to the time gating circuitry and signal processing 613.

Another slickline cable parameter that can be used to detect structural defects is dynamic strain variation. Dynamic strain variation can be determined by measuring a corresponding dynamic refractive index change under preset cable deformation or artificial strain amplitude. The dynamic refractive index, n, due to photoelastic effect, could be described by the equation:

$$\Delta n(t)/n \propto \in_m(t) + \in_{th}(t) \approx \in(t)$$

where the $\in_m(t)$ term comes from defects induced by mechanical strain, and $\in_{th}(t)$ term corresponds to thermal induced strain. Since temperature variation is a slow function in the downhole environment, the dominated strain is from tensile loading induced strain contribution. The baseline data can then be used to convert the measured signal to a relative dynamic strain amplitude.

Figure 7:
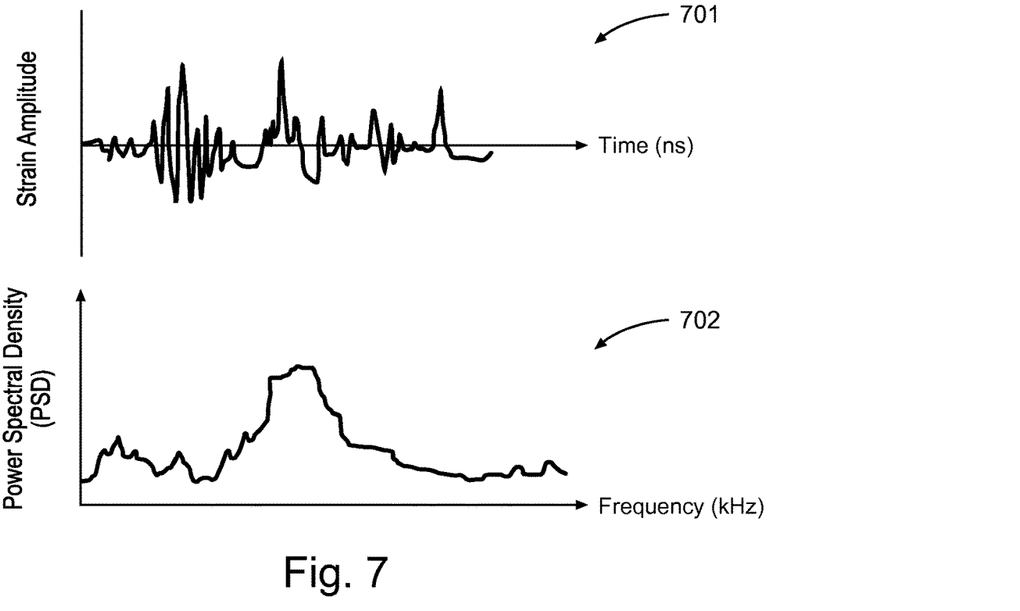
FIG. 7 illustrates plots of measured localized strain amplitude and power spectral density from coherent interference from time-domain scattering signals along the optical waveguide.

FIG. 7 illustrates one embodiment of a measured localized strain amplitude 701 and power spectral density 702 from coherent interference from time gated scattering signals as detected in FIG. 6. The strain amplitude graph 701 includes time along the x-axis and the strain amplitude along the y-axis. The strain amplitude depends upon the localized medium deformation induced by defects formation and propagation.

Slickline cable operation condition can be monitored by measuring the standard deviation range of the strain amplitude. A pre-calibrated range under specific strain amplitude can be used to evaluate the change between a peak strain amplitude and a predetermined maximum loading strength strain amplitude. A threshold of the peak strain can thus be defined such that a potential slickline cable failure can be determined.

Within the limited coherent length, the resonant frequency power spectral density (PSD), in the lower graph 702, could give a broad vibrational noise distribution from a section of the slickline cable. Some of signatures of the PSD can be used as a baseline for monitoring long-term cable reliability since tensile loading strain variation can strongly modulate localized cable mechanical response to loading dynamics with a specific power spectral density profile. Some spectral band signals from the observed power spectral density profile may be associated with the wireline tool, reel and mechanical system operation related noises, while other bands may be identified as slickline cable intrinsic signatures.

Figure 8:
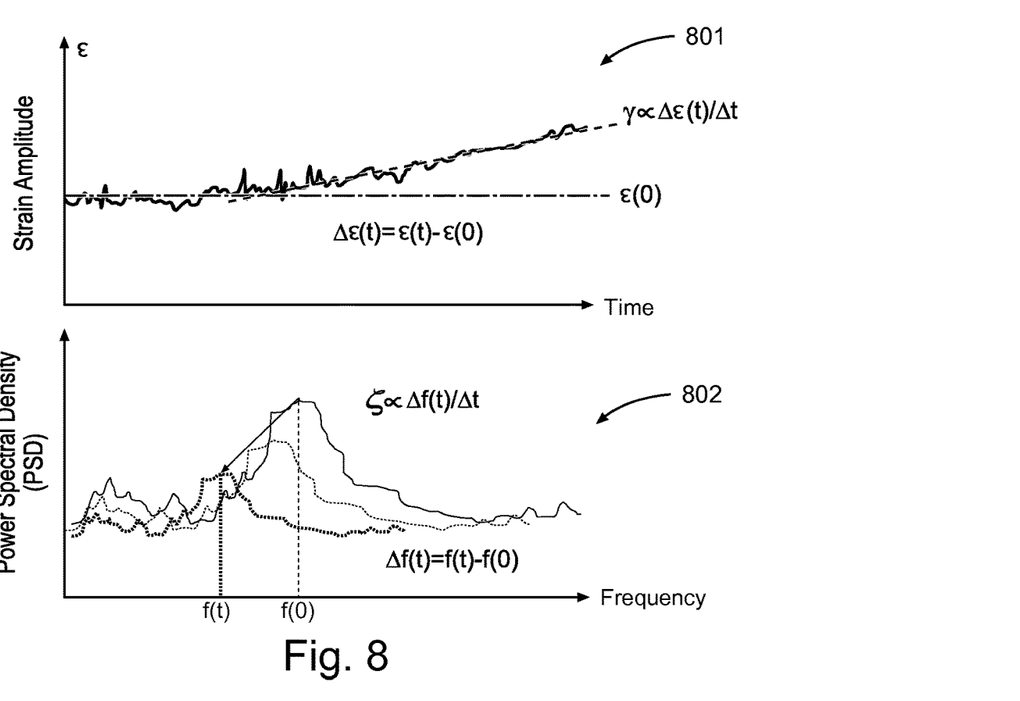
FIG. 8 illustrates plots of structural defect formation and growth rate at a specific slickline cable location.

The top graph 801 of FIG. 8 illustrates the strain amplitude versus time while the bottom graph 802 illustrates the PSD versus frequency. In one embodiment, the measured transient strain amplitude could vary with time. In another embodiment, the measured averaged strain amplitude could show a consistent trend as a function of time. The initial strain amplitude, $\in(0)$, and the measured strain amplitude, $\in(t)$, may suddenly increase at a specific time because of structural defects formation and growth during wireline tool loading time. The measured averaged strain amplitude trend can be illustrated by the equation:

$$\Delta\in(t)=\in(t)-\in(0)$$

Since the loading could be static or dynamic, the defects formation is also statistically accumulated from ignorable influence to obvious cable mechanical strength degradation. This time dependent strain amplitude variation rate, $\gamma$, can be characterized by the equation:

$$\gamma \propto \Delta\in(t)/\Delta t$$

The fast Fourier Transform (FFT) algorithm can be used to convert the time-domain strain amplitude variation to frequency-domain analysis by its PSD, where the specific localized resonant frequency signatures can be identified in the KHz to MHz range, which reflects the broad range of the defect size formation process.

The lower graph 802 of FIG. 8 illustrates one potential failure mode analysis method where the increased averaged strain amplitude is accompanied with a decrease in the coherent resonant PSD frequency. The decrease in frequency can be illustrated by the equation:

$$\Delta f(t)=f(t)-f(0)$$

where f(t) is the measured resonant frequency signature value and f(0) is the initial resonant frequency signature value. The negative $\Delta f(t)$ will reflect cable mechanical strength fatigue that is a result of structural defect creation.

Both the PSD amplitude and signature frequency show a decreasing trend. Since a frequency signature can be more reliable way of detecting a slickline cable failure mode, a time-dependent frequency variation rate, $\zeta$, can be defined by the equation:

$$\zeta \propto \Delta f(t)/\Delta t$$

This variation rate is associated with the structural defect growth. The initial resonant frequency signature value, f(0), could be defined at normal wireline tool loading condition. In practice, the time-dependent strain amplitude variation rate ($\gamma$) is combined with the time-dependent frequency variation rate ($\zeta$) to catch a slickline cable failure event during the wireline tool logging operation.

Since the spatial resolution of a coherent Rayleigh based acoustic signal detection is limited to al to a few meters, above time-domain and frequency-domain data analyses will be practically processed sectional cable by sectional cable length, at least starting from the pulley point to downhole logging tool end. In one embodiment, the acoustic signal detection may be at a few kHz range to evaluate general cable mechanical strength status across relative large length of the cable. In another embodiment, the acoustic signal detection may be at a few ten kHz ranges to evaluate specific location cable mechanical strength status. In another more embodiment a scheme of fast and slow mixing scanning method is used for cable structural defect detection for catching random defect creation events specifically during upward and downward tool logging processes.

Figure 9:
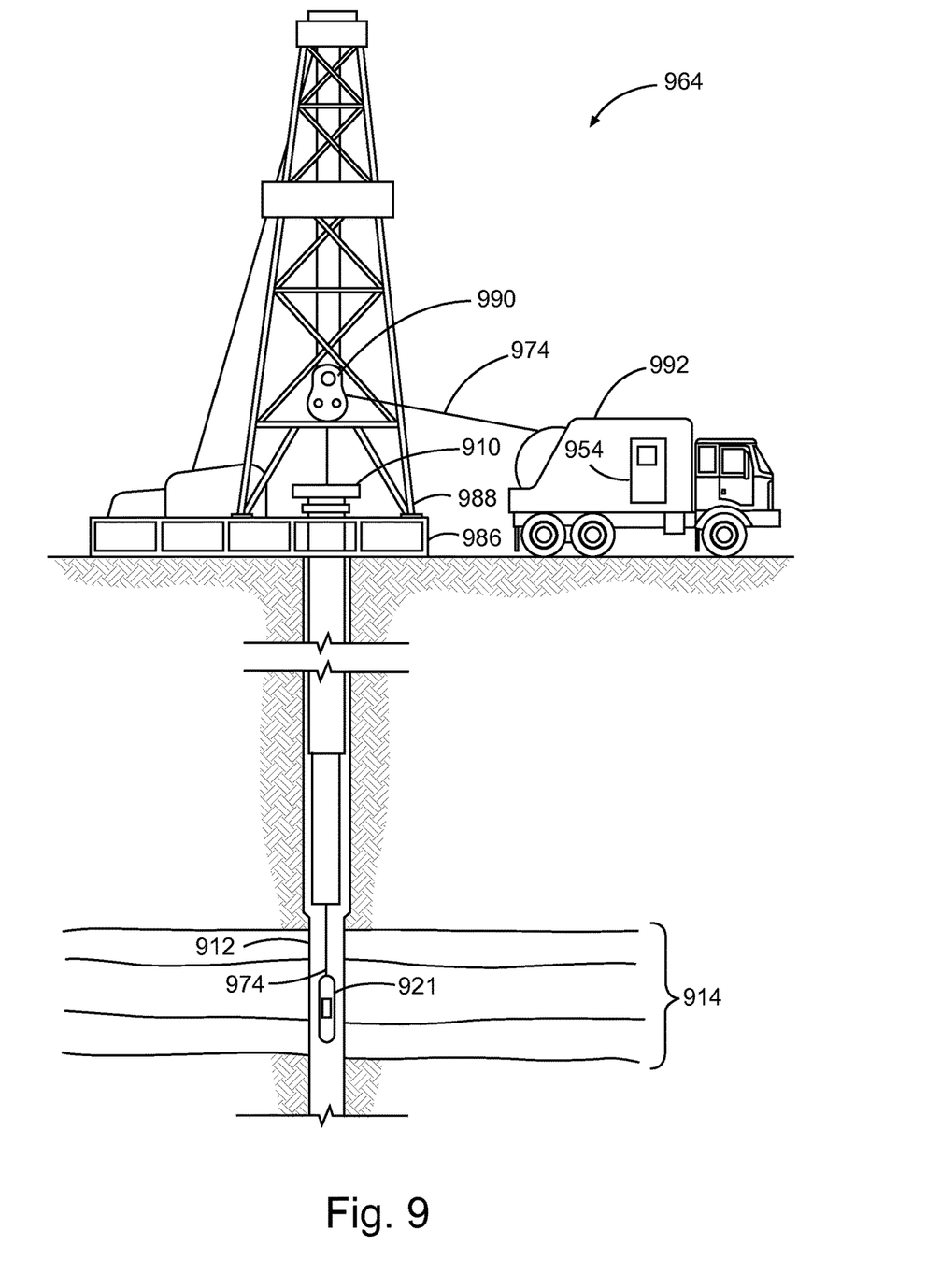
FIG. 9 illustrates an embodiment of a wireline system in accordance with various embodiments.

FIG. 9 illustrates a wireline system 964 embodiment. The system 964 may include portions of a wireline logging tool body 921, as part of a wireline logging operation. The slickline cable 974 can extend off a cable spool 920 and be coupled to the wireline logging tool body 921.

A drilling platform 986 is equipped with a derrick 988 that supports a pulley system 990. Drilling of oil and gas wells is commonly carried out using a string of drill pipes connected together so as to form a drilling string that is lowered through a rotary table 910 into a wellbore or borehole 912. Here it is assumed that the drilling string has been temporarily removed from the borehole 912 to allow a wireline logging tool body 921, such as a probe or sonde, to be lowered by slickline cable 974 into the borehole 912. Typically, the wireline logging tool body 921 is lowered to the bottom of the region of interest and subsequently pulled upward at a substantially constant speed.

During the upward trip, at a series of depths, the instruments (e.g., transducers and receivers) included in the tool body 921 may be used to perform measurements on the subsurface geological formations 914 adjacent the borehole 912 (and the tool body 921). The received data, that can include acoustic data, can be communicated to a surface logging facility 992 for storage, processing, and/or analysis as described previously. The logging facility 992 may be provided with electronic equipment for various types of signal processing.

In some embodiments, the tool body 921 comprises an acoustic tool for obtaining and analyzing acoustic measurements from a subterranean geological formation through a wellbore. The tool is suspended in the wellbore by the slickline cable 974 that connects the tool to a surface control unit 954 as described subsequently. The tool may be deployed in the wellbore on coiled tubing, jointed drill pipe, hard wired drill pipe, or any other suitable deployment technique.

In some embodiments, the slickline cable 974 passes through a packing assembly that isolates downhole high-pressure from surface pressure (not shown in above picture). In other embodiments, the slickline cable 974 proceeds through a blow-out-preventer (BOP). In addition, the system may include other elements that are used in slickline logging services. Loading strain can be induced from around the pulley section 990 and any transient strain can add static strain as well as loading strain. The tool body 921 may mean different downhole sensors or a sampling tester, which may use battery-powered instruments or use casing or the slickline cable 974 as an electrical connection. As a normal operation, the tool body 921 is hanging by the pulley system 990 such that the loading strain is accumulated around the pulley point as a "critical stress turning point" related to cable failures.

To monitor the cable internal strain variation and defect formation, the logging facility 992 can include a Structural Acoustic-Optical Defect Detection (SADD) System 954 connected to the slickline cable 974 from the end of the spool cable. The SADD system 954 interrogates the tensile strain variation from the full length of the slickline cable, with specific attention on a "critical strain turning point". At such a point, the transient and non-uniform loading induced structural defects could emit acoustic noises or localized strain waves, which are analyzed by the coherent interference technique. Structural defects, such as axial and radial cracks and delaminations can be identified by their high-frequency characteristics. The down-shift of the PSD is associated with defects growth and propagation.

Figure 10:
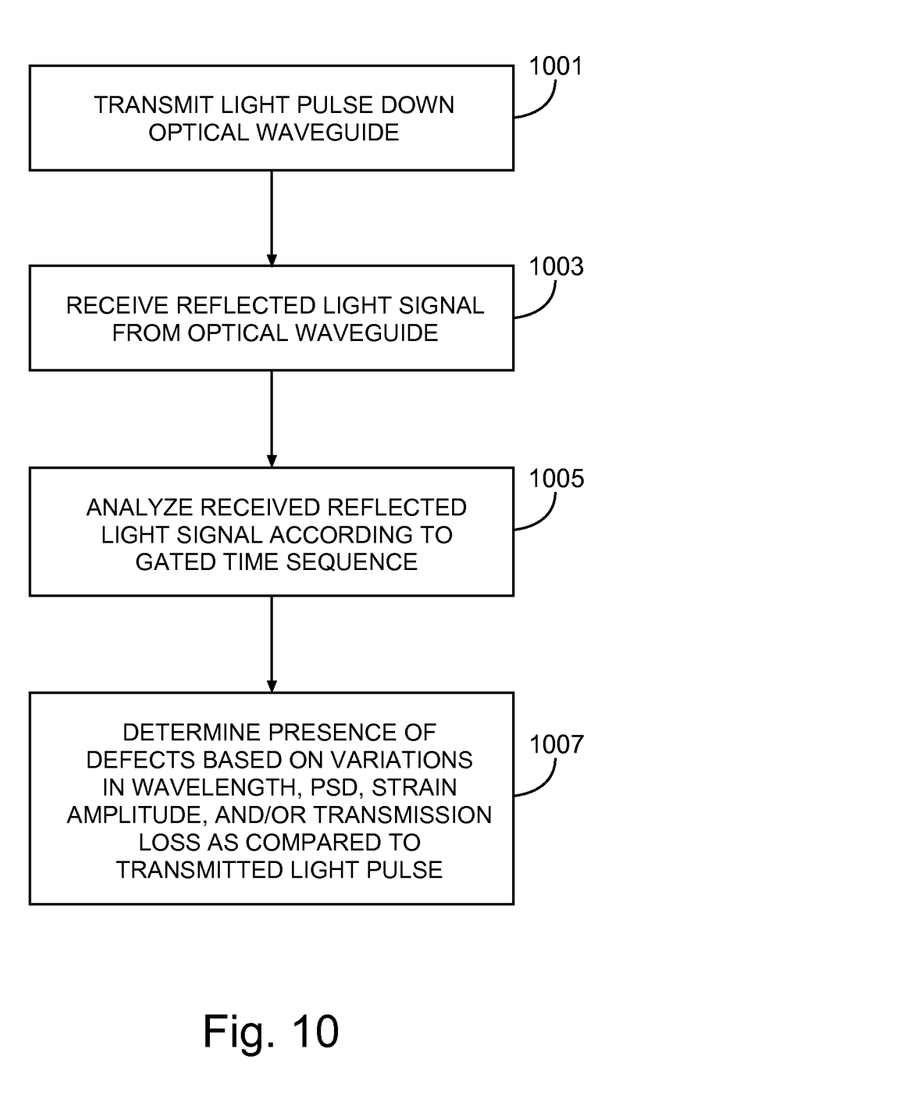
FIG. 10 illustrates a flowchart of an embodiment of a method for defect detection in a slickline cable.

FIG. 10 illustrates a flowchart of an embodiment of a method for detection of defects in a slickline cable. The method transmits a light pulse along an optical waveguide 1001. A reflected light signal is received (e.g., measured) from the optical waveguide 1003. The received reflected signal is analyzed according to a gated time sequence 1005.

The presence of defects can then be determined based on variations in scattering intensity, specific spectral signature, PSD, phase shift, strain amplitude, and/or transmission losses of the received reflected signal as compared to the transmitted light pulse 1007.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A distributed nondestructive inspection method for slickline cable structural defect detection, the method comprising:

transmitting a light pulse along an optical waveguide in the slickline cable;

receiving a reflected light signal from the optical waveguide in response to scattering of the light pulse; and detecting defects in the slickline cable based on variations in scattering intensity, phase shift, specific spectral signature, power spectral density, strain amplitude, and/or transmission loss of the reflected light signal as compared to the light pulse, wherein detecting the defects in the slickline cable comprises monitoring a standard deviation range of the measured strain amplitude.

2. The distributed nondestructive inspection method of claim 1, further comprising analyzing the reflected light signal according to a gated time sequence.

3. The distributed nondestructive inspection method of claim 1, wherein monitoring the standard deviation range of the strain amplitude comprises determining a change between a measured peak strain and a predetermined strain resulting from a loaded slickline cable.

4. The distributed nondestructive inspection method of claim 3, wherein determining the defects in the slickline cable comprises determining when the peak strain exceeds a predetermined threshold.

5. The distributed nondestructive inspection method of claim 1, wherein detecting the defects in the slickline cable comprises converting a time-domain strain amplitude variation to the frequency domain power spectral density based on fast Fourier transform algorithm from the measured strain amplitude.

6. A distributed nondestructive inspection method for slickline cable structural defect detection, the method comprising:

transmitting a light pulse along an optical waveguide in the slickline cable;

receiving a reflected light signal from the optical waveguide in response to scattering of the light pulse; and detecting defects in the slickline cable based on variations in scattering intensity, phase shift, specific spectral signature, power spectral density, strain amplitude, and/or transmission loss of the reflected light signal as compared to the light pulse, wherein detecting the structural defects in the slickline cable comprise detecting the defects in the slickline cable using both a time-dependent strain amplitude variation rate and a time-dependent frequency variation rate.

* * * * *